(12) United States Patent
Lipson et al.

(10) Patent No.: US 7,961,312 B2
(45) Date of Patent: Jun. 14, 2011

(54) CALIBRATED ANALYTE CONCENTRATION MEASUREMENTS IN MIXTURES

(75) Inventors: Jan Lipson, Cupertino, CA (US); Thomas J. Lenosky, San Jose, CA (US); Jeffrey M. Bernhardt, Santa Cruz, CA (US)

(73) Assignee: C8 Medisensors Inc., San Jose, CA (US)

( * ) Notice: Subject to any disclaimer, the term of this patent is extended or adjusted under 35 U.S.C. 154(b) by 322 days.

(21) Appl. No.: 12/191,096

(22) Filed: Aug. 13, 2008

(65) Prior Publication Data

US 2009/0079977 A1    Mar. 26, 2009

Related U.S. Application Data

(60) Provisional application No. 60/955,575, filed on Aug. 13, 2007.

(51) Int. Cl.
G01N 3/00 (2006.01)
G01N 3/44 (2006.01)
G01N 33/53 (2006.01)

(52) U.S. Cl. ....... 356/301; 356/300; 435/7.2; 435/288.4

(58) Field of Classification Search .......... 356/300–319, 356/244, 246, 432–444; 435/288.4, 288.7, 435/297.5; 600/316, 317, 332
See application file for complete search history.

(56) References Cited

U.S. PATENT DOCUMENTS

| | | | |
|---|---|---|---|
| 5,807,750 A * | 9/1998 | Baum et al. | 436/164 |
| 6,167,290 A | 12/2000 | Yang et al. | |
| 6,197,575 B1 * | 3/2001 | Griffith et al. | 435/288.4 |
| 6,330,064 B1 * | 12/2001 | Rieder | 356/481 |
| 7,003,337 B2 * | 2/2006 | Harjunmaa et al. | 600/316 |
| 7,286,222 B2 * | 10/2007 | Gardner, Jr. | 356/301 |
| 2003/0148391 A1 * | 8/2003 | Salafsky | 435/7.2 |
| 2006/0063993 A1 | 3/2006 | Yu et al. | |
| 2007/0049809 A1 | 3/2007 | Bechtel et al. | |
| 2007/0060806 A1 | 3/2007 | Hunter et al. | |

OTHER PUBLICATIONS

PCT International Search Report and Written Opinion, PCT/US2008/073045, Nov. 7, 2008. 11 Pages.
Brereton, R.G., "Chemometrics Data Analysis for the Laboratory and Chemical Plant," 2003, p. 199-204.
A. Phatak, S. De Jong, "The Geometry of Partial Least Squares," Journal of Chemometrics, 1997, pp. 311-338, vol. 11.
T. Ozeki, and N. Ogawa, "Inclusion of Chemical Constraints in Factor Analysis to Extract a Unique Set of Solutions from Spectroscopic and Environmental Data," Chemometrics and Intelligent Laboratory Systems, 2004, pp. 61-72, vol. 71.

* cited by examiner

*Primary Examiner* — Sang Nguyen
(74) *Attorney, Agent, or Firm* — Fenwick & West LLP

(57) ABSTRACT

The concentration of analytes in a complex mixture can be ascertained by spectroscopic measurement, even if the spectra of substances other than the analyte overlap with that of the analyte. Both independently measured concentrations of the analyte in a training set and of the analyte spectrum are used. Variances in the spectral data attributable to the analyte are isolated from spectral variances from other causes, such as compositional changes associated with different samples that are independent of the analyte. For the special case of noninvasive glucose measurements on the skin of biological organisms, the volume averaged glucose in the sample is predicted from the blood glucose. A test for over-fitting of the data is also described.

20 Claims, 9 Drawing Sheets

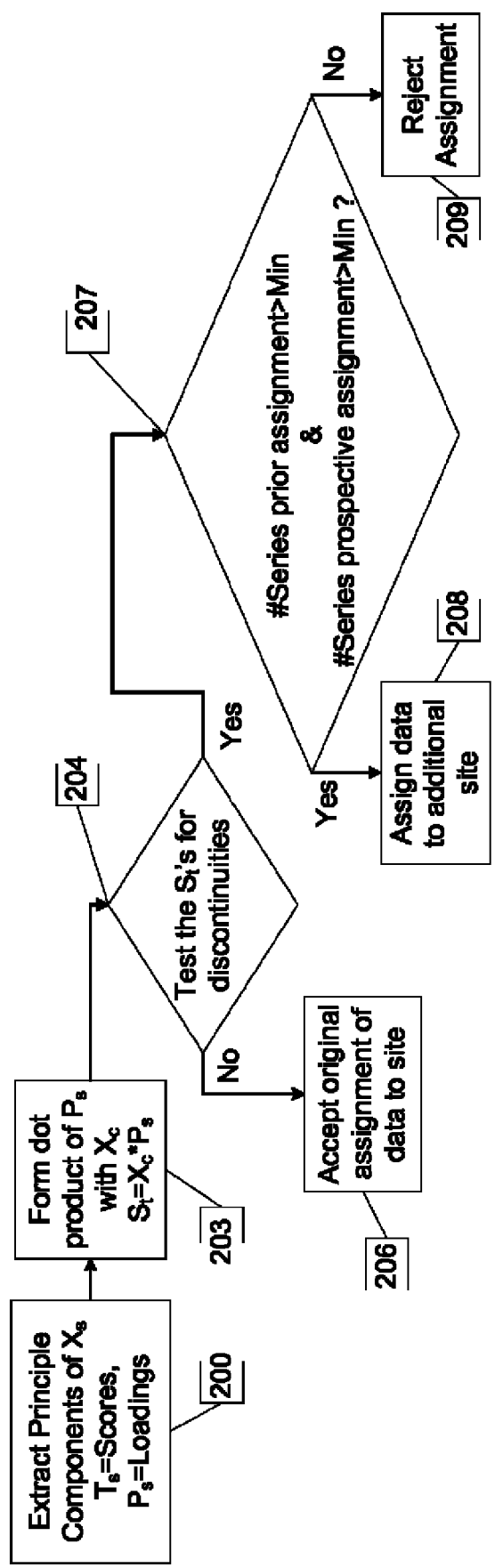
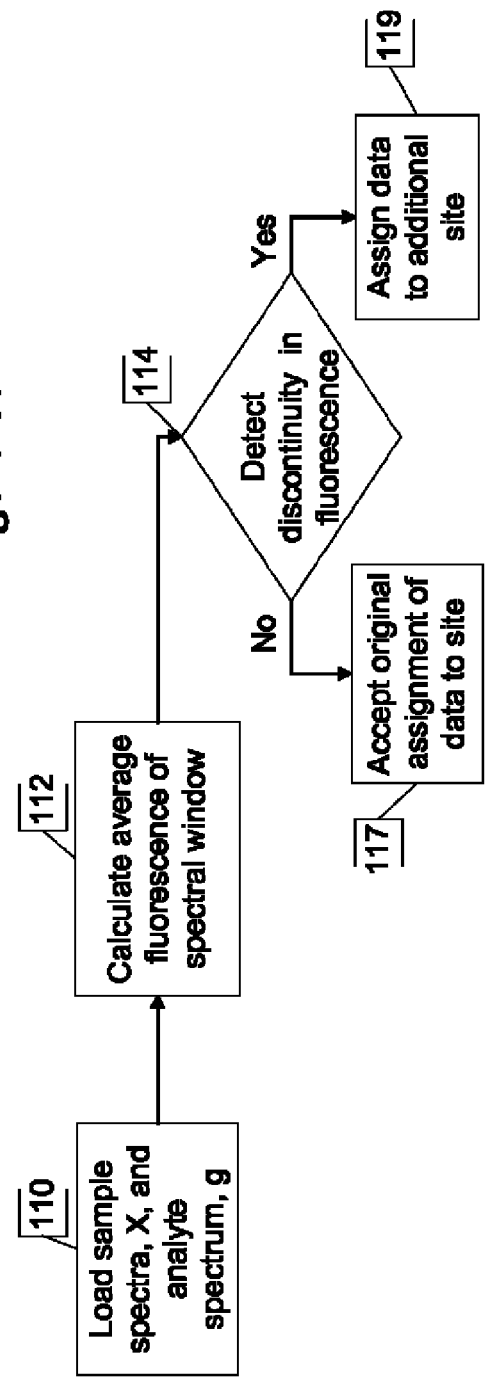
Figure 8a
Figure 8b

CALIBRATED ANALYTE CONCENTRATION MEASUREMENTS IN MIXTURES

CROSS-REFERENCE TO RELATED APPLICATION

This application claims priority under 35 U.S.C. §119(e) to U.S. Provisional Patent Application Ser. No. 60/955,575 "Calibrated Analyte Concentration Measurements in Mixtures," filed Aug. 13, 2007, the subject matter of which is incorporated herein by reference in its entirety.

BACKGROUND OF THE INVENTION

1. Field of the Invention

This invention relates in general to making calibrated measurements of analytes in samples, which are illuminated with electromagnetic radiation, so as to produce a scattered spectrum. Specifically, the invention permits determination of the concentration of an analyte in complex mixtures, wherein there is significant spectral overlap between the analyte and other compounds present in the sample.

2. Background and Relevant Art

The field of chemometrics is primarily devoted to mathematical techniques whereby the concentration or presence of a target analyte can be ascertained from data which contains signals from other compounds. A typical problem occurs when the data consist of spectra, and the sample consists of a mixture of compounds, one or more of the spectra of such compounds overlapping with that of the analyte of interest. In general, there are several classes of additional information which can be helpful in isolating the signal of the analyte. The spectrum of the analyte may be measured in advance in a sample which does not contain other compounds. Alternatively, if it is not convenient to measure the analyte by itself, a preparation can be made without the analyte, and the spectrum of this preparation ascertained. Then the analyte can be added to the preparation, and a second spectrum taken. When the first spectrum is subtracted from the second, the resulting spectrum should be that of the analyte. Similarly, the spectra of other compounds which are thought to be present in the sample can sometimes be measured beforehand.

In addition, it is sometimes possible to make an independent measurement of the concentration of an analyte in the sample by a second method. If multiple samples are available wherein independent measurements of the analyte have been made, and the analyte is present in differing concentrations in these samples, it may be possible to calibrate the spectroscopic data on the basis of these independent measurements. Then, when an additional sample is presented to the spectroscopic apparatus, wherein the concentration of the analyte is not known, the calibration obtained from the prior set of samples can be used to ascertain the concentration of the analyte in the new sample.

The set of samples wherein the concentration of the analyte has been ascertained by an independent method and which are used to create the calibration of the spectroscopic apparatus is called the "training set." The new sample or samples wherein the concentration of the analyte is unknown is called the "test set." The spectra of the analyte or of other substances present in the samples may or may not be known.

A common means of ascertaining whether the calibration will properly predict the concentration of an analyte in a new sample is called "cross-validation." In this process, the concentration of the analyte in all the samples is measured by independent means. The set is then segmented into two subsets. One of the two subsets consists of the training set and the other subset will be the test set. The concentration of the analyte in the test set is predicted by the calibration which is obtained from the training set. These predictions can then be compared with the actual, independently measured concentration of the analyte in the test set. The assignment of samples to either the training or test sets can be permuted in many patterns, hence, the concentration of the analyte in every sample or subset of samples can be predicted by the remaining samples.

A number of basic algorithms have been developed to create a calibration based on data from a training set. Let the matrix X consist of spectra from the multiple samples. Let Y be the independently measured concentrations of the analyte or analytes in each sample. If there is one analyte which has been measured independently, Y is a vector consisting of concentration versus sample. If multiple analytes have been independently measured, then Y is a matrix. The purpose of the algorithm is to calculate a model which when applied to new spectra from a new sample will correctly predict the concentration of the analyte or analytes of interest. An adequate treatment of the basic approaches can be found in "Multi-Way Analysis," by A. Smilde, R. Bro, and P. Geladi, Pub. John Wiley and Sons, 2004, ISBN-0-471-98691-7.

If the spectra of all the compounds in the mixture are known then it is sometimes possible to use ordinary regression to extract the concentration of any one of the compounds from a spectrum of the mixtures. Even in this case, the regression may be ill-conditioned because the spectra of the substances will not, in general, be an orthogonal set. In regression, when the independent variables are partially colinear, the error in the weights assigned to the independent variables may be excessive. Also, in many important cases, the spectrum of every compound in the mixture may not be known. Frequently, some of the significant compounds in the mixture have not been identified.

To resolve the problems associated with ordinary regression, a variety of techniques have been developed that do not rely on a priori knowledge of the spectra of the compounds in the mixture. In principle components analysis, the following decomposition of the data is made:

$$X_{ij} = \sum_{p=1}^{ncomp} P_{ip} T_{jp} + \varepsilon_{ij} \qquad (1)$$

where the $P_{ip}$ are called the "loadings," the $T_{jp}$ are called the "scores," and $\varepsilon_{ij}$ is the residue after the specified number of components are derived. In our convention, the loadings will be spectra and the scores will be sample sequences, which for example, may be time series. The $P_{ip}$ are an orthonormal set, and the $T_{jp}$ are an orthogonal set. The number of components for the decomposition is ncomp. This method is standard principal component decomposition, a well known method, which is described for example in Principal Component Analysis, I. T Jolliffe, 2004, ISBN 0-387-95442-2.

In general, the loadings $P_{ip}$, are not the spectra of compounds in the mixture. The principle components are not unique in providing a basis for the plane of closest fit to the data, X. The loadings, P, can be rotated in the plane of closest fit, so while the plane is unique, the basis vectors that describe it are not. Therefore, since the P's can be rotated to make a decomposition of equally low error, these spectra can have no inherent relation to the actual spectra of the compounds. Furthermore, it has already been noted that the spectra of the compounds are not, in general, orthogonal, whereas the P's are orthonormal by construction.

It is possible to use the scores, T, in regression, a technique known as principle components regression. The advantage is that the T's are orthogonal so that the regression will not be ill-conditioned.

Another example of a technique requiring no a priori knowledge of the spectra of the compounds is that of partial least squares regression, a rigorous discussion of which is found in "The Geometry of Partial Least Squares," A. Phatak, S. De Jong, Journal of Chemometrics, Vol. 11, pgs. 311-338 (1997). The algorithm minimizes the error of estimation of the spectral data, and of the independently determined concentrations iteratively.

One serious difficulty with the above mentioned techniques is the danger of over-fitting the data. Over-fitting in this context is defined as either training the method based on spurious correlations in the data, or else training the method based on other analytes which are correlated with the target analyte. In either case, the problem arises because the data contains limited information about the true analyte while containing a rich enough set of interfering substances or signals. In practice, the set of data Y, which is being fit is not very complex in the sense that it could be adequately represented mathematically by relatively few parameters. The probability of obtaining spurious correlations with one or more the components extracted in the decompositions of the data is then not negligible. A calibration constructed from over-fitting will have impaired predictive accuracy for new data. In particular, in the latter case mentioned above, calibration to correlated analytes, the correlation may not be guaranteed to hold under all conditions of interest, while in the former case there is not even the possibility of a correct determination.

The difficulty may be viewed in terms of the algorithm being under-constrained, permitting spurious solutions which nevertheless model the data in the training set. Alternatively, we may say that in such circumstances it may be necessary to make more measurements so that the data being fit becomes increasingly complex. The required number of such measurements, may, however, be impractically large.

It is possible to impose constraints on the decompositions of the data, on the basis that the spectra must obey certain rules. A simple case would be to require that the loadings be non-negative. See, for more such examples, "Inclusion of Chemical Constraints in Factor Analysis to Extract a Unique Set of Solutions from Spectroscopic and Environmental Data," T. Ozeki, and N. Ogawa, Chemometrics and Intelligent Laboratory Systems, Vol. 71, pgs. 61-72 (2004). For mixtures of sufficient complexity, however, these constraints are generally too weak to be sufficient.

It is notable that the techniques that are described above were developed for the case where none of the spectra were known in advance, yet sometimes one or more of the spectra of the compounds in the mixture are in fact known. Such a priori knowledge is in principle very useful in avoiding over-fitting, however, those algorithms which were designed for data sets where no such knowledge was available do not in general have an appropriate way of incorporating specific spectra.

In some cases, it is observed that there are sources of variance in the measured spectra of a mixture which are not related to the variances of the analyte concentration in the mixture. An example of such a case is the Raman spectra of human skin, when it is desired to measure the concentration of one or more analytes such as glucose. It is found that different sites on the skin contain significantly different concentrations of other compounds besides glucose, whose spectra overlap, in part, with that of glucose. Further, there are compositional differences between the skins of individual human beings. Existing algorithms do not provide a means of extracting these irrelevant sources of variance which can confound the measurement of the target analyte.

BRIEF SUMMARY OF THE INVENTION

These and other limitations are addressed by the present invention, whereby the concentration of specific analytes can be determined by analysis of the composite spectrum of a mixture, and spectral variances of multiple samples that arise from sources other than the varying concentration of the analyte can be extracted. In one embodiment of the invention, a method to mitigate the potential hazard of over-fitting for insufficiently complex data is used.

The fundamental strategy of the proposed algorithm is to isolate the predominant contribution of the target analyte in the collected spectral data to a single independent variable, and to create other appropriate independent variables which describe the variances in the observed spectra from sources other than the variations of the target analyte concentration. It is a further objective of the algorithm to reduce the colinearity of the independent variables so that subsequent regression will be well-conditioned. Additionally, it is a further objective of the algorithm to produce an adaptive regression for calibration that depends on variation in both the training and test data sets. Finally, it is a further objective of the algorithm to increase the apparent complexity of the data being fit so as to reduce the probability of over-fitting.

In one embodiment, the spectral data consists of a series of spectra obtained on a series of different samples, where the number of distinct spectra obtained on each sample can be different. The concentration of the analyte of interest can change during the process of obtaining the spectra; that is, the concentration changes while taking a series of spectra on any given sample and also changes when moving from one sample to the next. The concentration of the target analyte is measured by a means independent of the spectroscopic apparatus, e.g., by an independent reference instrument, so as to create a suitable training set. The proposed algorithm creates a calibration which depends on both the training and the test data, and which can then be applied to predict the unknown analyte concentration for the test spectral data.

An estimate of the concentration of the analyte, $\hat{Y}$, subject to a scaling factor, is obtained by forming the dot product of the spectral data set X with the spectrum of the analyte, g, which was obtained a priori. The data set X (which contains both training and test spectral data) is then modified to create a new data set, $X_f$, where the analyte spectrum, g, has been projected out of X. A new set, $X_s$, is now created from $X_f$ by taking the mean of a subset of the spectra for each sample. One preferred embodiment would be to choose the subset to be the first n spectra in each sample, but many other choices are also possible. The mean sample spectra are intended to capture the sample to sample variance of the spectra not associated with different concentrations of the analytes since the sample spectra are created from a data set where the analyte spectrum has been projected out. Principle components of $X_s$ are then extracted with the scores being $T_s$. These scores, $T_s$, are then projected out of the set $X_f$, resulting in the set $X_g$. It is then expected that $X_g$ will contain variance information which is associated neither with the varying concentrations of the analyte, nor with the sample to sample variance not associated with the varying concentrations of the analyte. For example, $X_g$ will contain variances associated with changes that occurred during the taking of multiple spectra on each sample, except for those changes associated with the changing concentration of the analyte. The principle components of $X_g$ are extracted creating the scores $T_g$. It is then possible to perform a regression against the independent measurements of the analyte concentration, Y, using the independent variables $\hat{Y}$, $T_g$, and $T_s$.

In another embodiment, noise terms are added both to X and Y. The noise term added to X has both a multiplicative scaling factor, and is further multiplied by the analyte spectrum, g. The cross-validated error of the estimation has a distinct minimum for the proper choice of scaling of the noise term added to the data X, and it is shown that the probability of over-fitting is substantially mitigated.

Additional features and advantages of the invention will be set forth in the description which follows, and in part will be obvious from the description, or may be learned by the practice of the invention described herein. These and other features of the present invention will become more fully apparent from the following description, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 8a is a method for automatically detecting that the sample presented to the apparatus has changed. FIG. 8b is an alternate scheme which is useful for detecting changes for samples that exhibit substantial photo-bleaching.

DETAILED DESCRIPTION OF THE PREFERRED EMBODIMENTS

Figure 1:
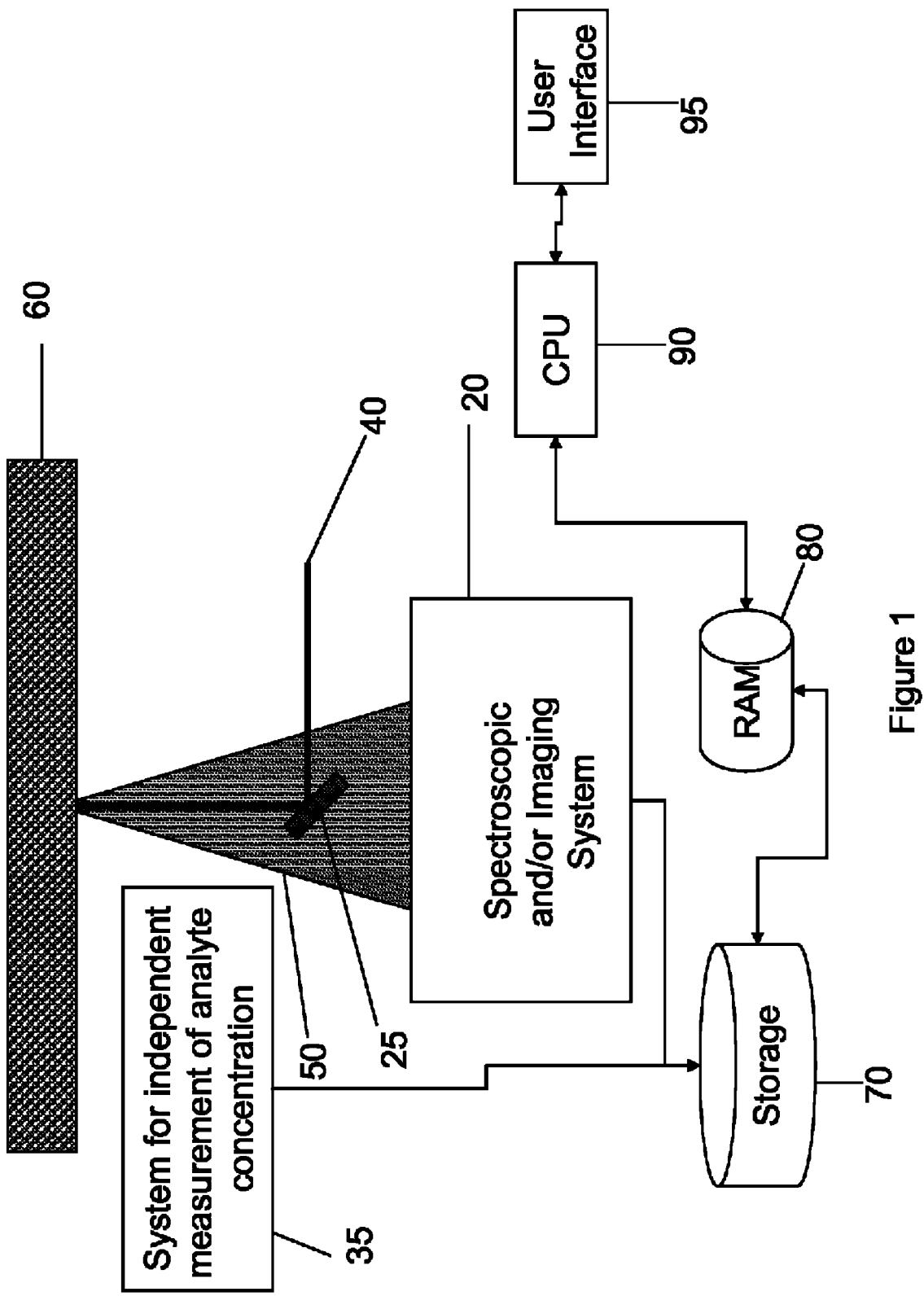
FIG. 1 is a block diagram of a system for measuring the spectra of samples, and for making independent measurements of analyte concentration, and wherein a calibration is calculated such that the concentration of the analyte can be computed from the spectra for a new sample where the concentration of the analyte is not known, in accordance with one embodiment.

FIG. 1 is a block diagram illustrating a system for measuring the spectra of samples in accordance with an embodiment of the invention. A light source 40 illuminates a sample 60 by means of a turning mirror 25. Light scattered from the sample 50 is created by combinations of elastic and inelastic scattering processes within the sample 60. Some of the scattered light is intercepted by the spectroscopic and/or imaging system 20 which contains a detector that converts the optical input to electronic output. The electronic output is transferred to storage 70, which may be for example a hard disk drive. In one embodiment, the algorithm which will perform the calibration also resides on the storage unit 70. In addition, the spectra of one or more substances believed to be present in the sample may reside on the storage unit 70. A system for making an independent measurement of the concentration of one or more analytes 35 also uploads its output to the storage unit 70. Random access memory 80 can receive any of the information from the storage unit 70 and CPU 90 can perform operations associated with the algorithm. A user interface 95 allows an operator to initiate the algorithm and to view the results of its output.

The apparatus of FIG. 1 is suitable for creating both training and test sets. To create a training set, multiple samples 60 are presented sequentially to the apparatus. The samples should contain differing concentration of one or more analytes of interest. One or more optical spectra are taken from each sample presented to the apparatus. The concentration of the one or more analytes of interest in each sample should not change significantly during the course of taking a single spectrum, however, their concentration may change during the course of taking multiple spectra. It is not necessary that the same number of spectra be taken on each sample. Independent measurements of the concentration of one or more analytes must be made. If it is known that the concentration of these analytes will not change significantly during the process of taking one or more spectra of the sample, these independent measurements can be made in advance. If, on the other hand, it is expected that the concentrations of the target analyte or analytes will change during the taking of one or more spectra, the independent measurement should be made sufficiently frequently so as to detect significant changes in the concentration of the analyte or analytes.

The case of making a noninvasive glucose measurement on the skin of human patients illustrates the proper order of operations. The measurements are made such that the subjects blood glucose levels will vary significantly during their course. This can be accomplished by deliberately manipulating these levels by administration of glucose, or insulin, or both. Alternatively the measurements can be made over extended periods of time, such as hours, days or weeks, when it is known that glucose levels will change appreciably. One or more spectra are taken from a specific area of the subject's skin, which shall be referred to as a site. If it is known that the glucose will be changing it is advantageous to take multiple spectra at each such site. Over the course of the measurements, however, it is advantageous to collect multiple spectra from multiple sites on the skin. The blood glucose is independently measured by another apparatus, such as those wherein a blood sample is extracted from the subject and subjected to chemical analysis. The blood samples should be taken such that they correspond in time to the taking of the spectra within a tolerance of about 5 minutes. A suitable training set is constructed from measurements on at least 3 sites and preferably on at least 6 sites, and where the blood glucose varied by at least 50 mg/dL, and preferably at least 100 mg/dL during the course of the sampling. However, other numbers of sites and variations of blood glucose can also be used to construct a training set. It is generally advantageous to take multiple spectra on each site. This is particularly so if significant changes in blood glucose are being deliberately produced for the purpose of obtaining the calibration. In this particular example, it is advantageous to perform Raman spectroscopy, although the algorithms described are not specific to this technique. Any method of spectroscopy wherein a spectrum is available is a potential candidate for the methods of measurement which are presented, and the techniques described herein are not specific either to biological organisms or any particular analyte unless specifically noted.

Preferably, each skin site is considered a separate sample (or possibly multiple samples, as described below). After the calibration is determined by running the calibration algorithm on the training set the blood glucose concentrations can be estimated for a new sample or samples, which are referred to as the test set wherein the concentration of glucose in the blood is not known, by applying the calibration to the new spectral data.

Figure 2:
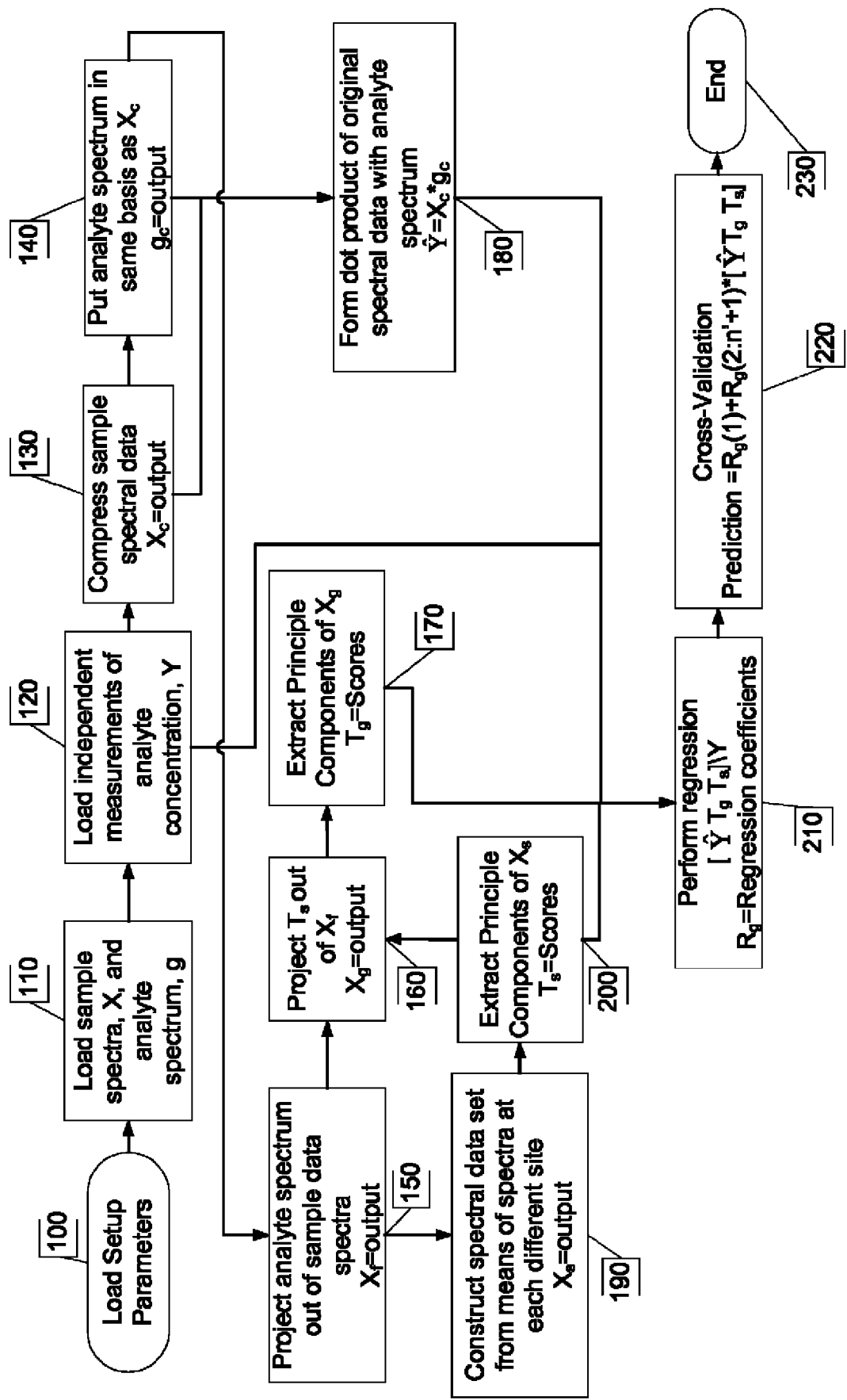
FIG. 2 is a flow chart showing a method for creating the calibration from spectral data and from independent measurements of the analyte concentration, in accordance with one embodiment.

An algorithm suitable for computing the calibration is presented in FIG. 2. The sequence of operations is not important except as will be noted below. In step, 100, setup parameters are loaded. In general, this is administrative information relating to identity of the sample. In step 110, the spectra for both the training set and the test set are loaded into the matrix variable, X. If multiple spectra are taken on multiple samples, it is necessary to keep track of which spectra correspond to which sample. Such information can be part of the administrative data loaded in step 100 or can be loaded in step 110. Also loaded in step 110, is the spectrum of a target analyte, g. In step 120, the independent measurements of the concentration of the analyte whose spectrum was loaded in step 110 are also loaded. In step 130, the spectral data are compressed to improve computational efficiency and to remove noise. An advantageous means of performing the compression is to extract the principle components and accept only the first N of these components in reconstructing the data, where N is chosen to optimize computational efficiency and the quality of the predictions. Particularly useful is to present the compressed data, $X_c$, in the spectral basis of the loadings of the principle components that are accepted. That can greatly reduce the dimension of the matrix $X_c$ in the spectral domain. If a new basis is introduced for the spectral data, the analyte spectrum should be put into the same basis, and the revised spectrum is called $g_c$ which is g•P, where the P are the loadings of the principle components of X, as is shown in step 140.

In step 150, the spectrum $g_c$ is projected out of the data $X_c$ as follows:

$$X_f = X_c - (X_c \cdot g_c) \otimes g_c \quad (2)$$

The spectral data set $X_f$ is then orthogonal to the analyte spectrum.

In step 190, the set $X_f$ is now used to create another set $X_s$. The set $X_s$ is the mean spectrum of the first several spectra, nsp, taken on each sample. Alternatively, it can be the sum of the first nsp spectra, however it is necessary to be consistent in using the same number of spectra for each sample to construct $X_s$. If only a single spectrum was taken on a sample, the spectrum of that sample in $X_s$ is just that single spectrum. The set $X_s$ is expected to capture the spectral variance associated with each sample that is not attributable to different concentrations of the target analyte. This is so, because the analyte spectrum has already been projected out of the data that is used to create $X_s$.

In step 200, the principle components of $X_s$ are extracted, creating the scores $T_s$. In step 160, the scores $T_s$ are projected out of $X_f$ as follows:

$$X_g = X_f - T_s * \text{pinv}(T_s) * X_f \quad (3)$$

where $\text{pinv}(T_s)$ is the Moore-Penrose pseudo-inverse of $T_s$.

The purpose of projecting out the subspace $T_s$ of the scores of $X_s$ is to remove the sample to sample variance that is not attributable to changes in the analyte concentration. The set $X_g$ should contain only the spectral variances associated with neither the sample to sample variation, nor the variances associated with the differences in the analyte concentration. An example of such variances might be changes which transpired in the samples over the course of taking multiple spectra, provided those changes are not associated with the analyte concentration. Such variations can be induced by the process of measurement as for example photo-bleaching produced by the light source, or the temperature of the sample may be changed by the light source or by other causes. Physical pressure on the sample can also be a source of such variations.

In step 170, the principle components of $X_g$ are extracted creating the scores $T_g$. One advantage of step 160 is that the scores $T_s$ will be substantially orthogonal to the scores $T_g$.

In step 180, the estimate $\hat{Y}$ is obtained by taking the dot product of the data set $X_c$ with the analyte spectrum as follows:

$$\hat{Y} = X_c * g_c \quad (4)$$

The spectra $X_c$ arise directly from the data set, and nothing has been projected out. Therefore, the estimate $\hat{Y}$ is expected to contain appreciably all the signal from the analyte, however, it is expected also to contain signal from any other substances whose spectra overlap with that of the analyte.

In step 210 we perform the regression:

$$R_g = [\hat{Y} T_g T_s] \backslash Y \quad (5)$$

where the symbol '\' is used to indicate linear regression, using the independent variables preceding the '\' symbol upon the dependent variable following it. The regression of Eq. 5 generates regression coefficients, $R_g$, the first of which is a constant term that is additive in creating the prediction. It can be seen that the orthogonality of the $T_g$'s to the $T_s$'s is advantageous in keeping the regression in Eq. 5 well conditioned. The basic idea behind the regression is that $\hat{Y}$ is a zeroth order estimator for the analyte concentration, and a linear combination of the $T_g$'s and $T_s$'s is used to form a correction. In order for the regression to be well-behaved, it is necessary that the set of regression terms is not linearly dependent. The $T_g$'s and $T_s$'s are automatically an orthogonal set based on their method of construction, however the variable $\hat{Y}$ is not necessarily orthogonal either to the $T_s$'s or the $T_g$'s. The reason the colinearity is not generally severe enough to be detrimental in regression is that $\hat{Y}$, which is a zeroth order estimator for the analyte concentration, is not likely to be colinear with any linear combination of the $T_g$'s and $T_s$'s, since they were formed from sets where the analyte spectrum was projected out.

In step 220, cross-validation is performed. Cross-validation is a well-known procedure in which a portion Q of the data is used to generate a calibration from which the analyte concentrations are predicted for the remaining data. Q can be set to different permuted subsets of the data, so that each datum is predicted at some point. An error metric based on the quality of the predictions quantifies the quality of the calibration and is also somewhat indicative of over-fitting or the lack thereof. For further explanation on this point, see *Chemometrics Data Analysis for the Laboratory and Chemical Plant*, Brereton, R. G., 2003, 199-204.

To perform cross-validation, step 220, a subset of the training set is extracted as a new training set, while the remainder is designated as the test set. The new training set is then used to predict the test set, and residuals are computed with respect to the actual independently measured analyte concentrations of the test set. The prediction, Ypred, is given by:

$$Ypred = R_g(1) + R_g(2:n'+1) * [\hat{Y} T_g T_s] \quad (6)$$

where $R_g(2:n'+1)$ is a vector of regression coefficients beginning with the second coefficient and running to the last coefficient, and n' is the number of columns in the independent variable matrix $[\hat{Y} T_g T_s]$, and $R_g(1)$ is a constant obtained from the regression of step 210. The members of the test set and training set can be permuted until all of the set has been predicted by the remainder. If the residuals are satisfactory, the calibration is obtained in a similar manner using the entire training set for training. To do so, the independent variables $[\hat{Y} T_g X_s]$ are calculated from the new spectral data using the method of FIG. 2. Then the previously calculated regression coefficients $R_g$ are applied to the new independent variables per Eq. 6, producing an estimate of the concentration of the analyte, and the method ends 230.

It is obvious from the foregoing that the method of FIG. 2 is readily generalized to multiple analytes. If a calibration for more than one analyte is sought, then independent measurements must be made on the additional analytes, and the variable Y will now be a matrix of such measurements. Similarly the analyte spectrum, g, can be generalized to a matrix of analyte spectra.

In some circumstances, it is not practical to obtain a very large number of observations of the concentration of the target analyte or analytes in multiple samples. Also, in some cases, the observations are made as a time series, and the measurements are correlated over an appreciable time frame. In such case the true information content of the data to be fit can be relatively small. A serious hazard of over-fitting of data exists when the information content of the independent variables is of the same order or greater than the information content of the data to be fit. Calibrations which arise from over-fit data may have impaired predictive capability for new samples.

It is possible to augment the information content of the data to be fit by adding a noise term. In such a case a random perturbation can be added to the variable Y so that:

$$Y_n = Y + n(t) \quad (7)$$

where n(t) is a noise term which varies between different observations of Y. If those observations are most conveniently ordered in time, then t can be time. Otherwise t may be an ordinal number such as the $17^{th}$ measurement in the set.

If the concentration of the analyte had in fact varied according to Eq. 7, the spectral data would be expected to have also been augmented according to:

$$X_n = X_c + S * n(t) * g_c \quad (8)$$

where S is a scalar. The appropriate value of S can be calculated on the basis of minimizing the cross-validated error of prediction.

Figure 3:
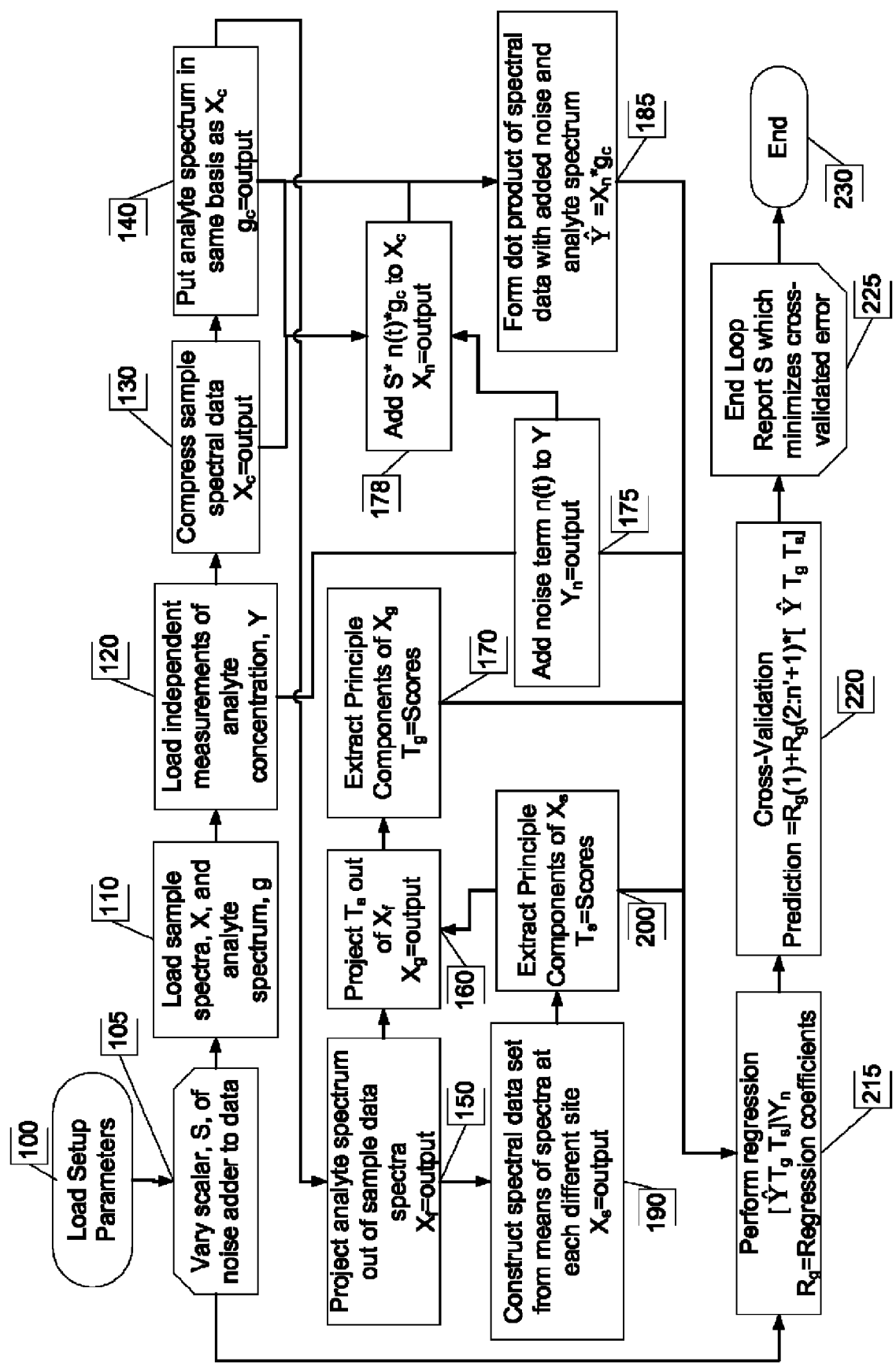
FIG. 3 depicts a preferred embodiment in which noise terms are added both to the data and to the independent estimates of the concentration.

An algorithm which implements the calculations presented in Eqs. 7 and 8 is shown in FIG. 3. An additional step, 105 is implemented which is a loop wherein a sequence of different trial values of S are presented to the remainder of the algorithm. Equation 7 is implemented in step 175, and Eq. 8 is implemented in step 178. In step 225, the value of S which minimizes the cross-validated error of prediction is ascertained and the loop begun in step 105 is terminated. It is found in practice that the method of FIG. 3 results in improved prediction accuracy, and the solutions from it are robust with respect to over-fitting.

Instead of projecting g out of $X_c$ in step 150 of FIG. 2, it is possible to project out the independently measured concentration of one or more analytes, Y as follows:

$$X_y = X_c - Y * \text{pinv}(Y) * X_c \quad (9)$$

Figure 4:
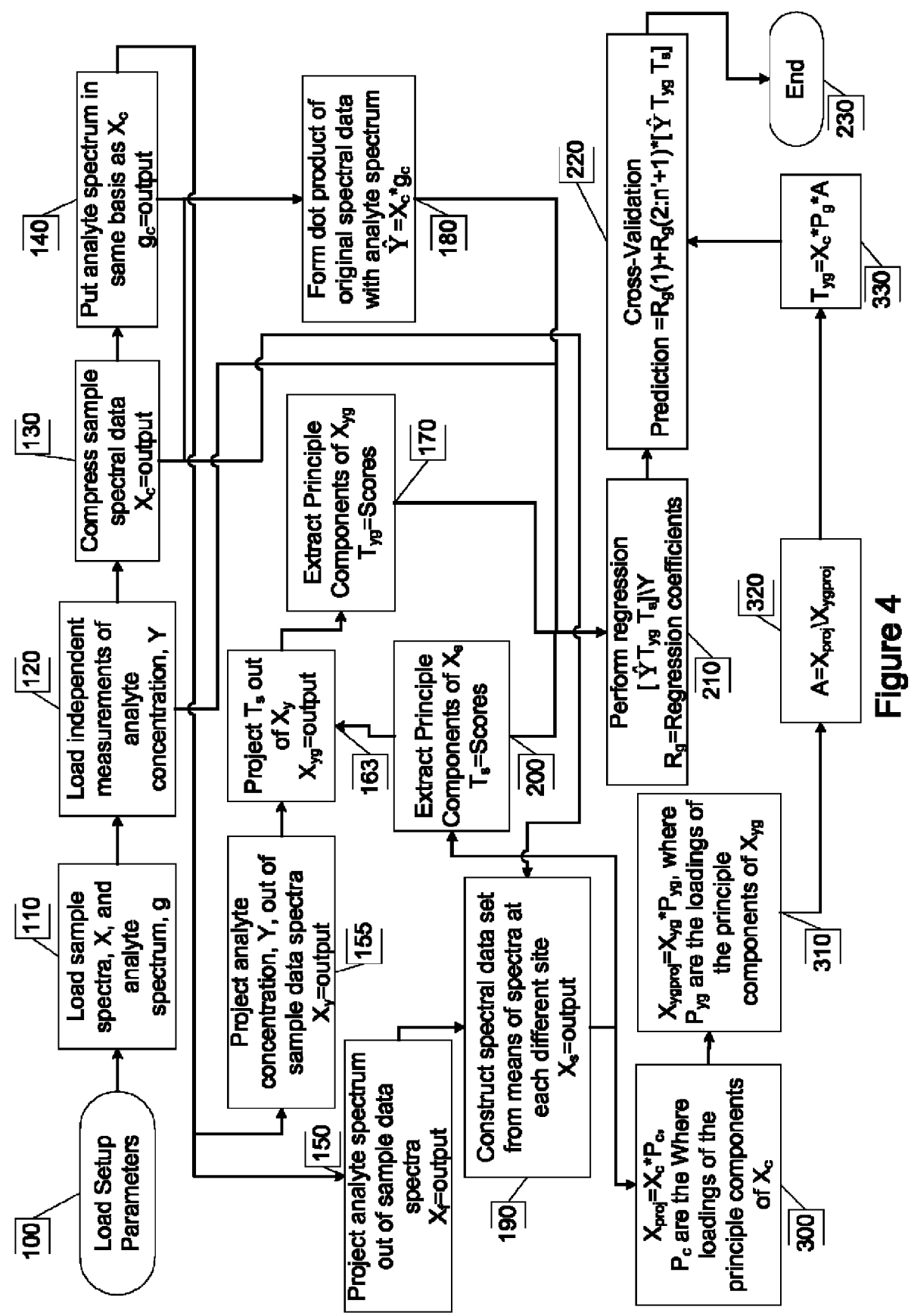
FIG. 4 is a flow chart of another preferred embodiment in which the independently measured analyte concentration is projected out of the spectral data as opposed to the analyte spectrum.

The logic of the projection of Eq. 9 is similar to that of projecting out the spectra, in that the objective is to create a set which contains a minimum of signal from the analyte or analytes. A special issue, however, arises when one projects out Y, because for the test set, one is not entitled to know Y. In consequence, the computation of Eq. 9 is not possible in the cross-validation, and we must find another way get the scores (the equivalents of $T_g$) that we need for the regression of step 220 in FIG. 2. FIG. 4 illustrates one alternative method. In the cross-validation, the computation may proceed as follows:

$$X_{proj} = X_c * P_c \quad (10)$$

where the $P_c$'s are the loadings of the principle components of $X_c$. Also we project $T_s$ out of data as before:

$$X_{yg} = X_y - T_s * \text{pinv}(T_s) * X_y \quad (11)$$

Then we also define:

$$X_{ygproj} = X_{yg} * P_{yg} \quad (12)$$

where the $P_{yg}$'s are the loadings of the principle components of $X_{yg}$.

We then form the regression:

$$A = X_{proj} \backslash X_{ygproj} \quad (13)$$

And in the cross-validation we may now compute:

$$T_{gy} = (X_c * P_{yg}) * A \quad (14)$$

where it can be seen that we have not anywhere included information about Y in the computation of the $T_{gy}$.

We are free to choose the number of components used in Eqs. 10 and 12, which may be different from each other. FIG. 4 illustrates the use of the foregoing. Equations 9, 10, 11, 12, 13, and 14 are implemented in steps 155, 300, 163, 310, 320, and 330 respectively.

Yet another alternative consists of using the output of step 155 to create $X_s$ in step 190, rather than the output of step 150. If this is done, we must find an alternative way to compute $X_s$ in the cross-validation, for now it can be seen that we have used Y to compute $X_s$, which we are not entitled to know in the cross-validation. The procedure in the cross-validation requires us to derive the scores that are analogous to $T_s$ in the regression 220, and we can proceed in the same manner as was done in Eqs. 10, 12, 13, and 14 for finding the scores, $T_{gy}$, that were analogous to $T_g$.

If the analyte spectrum is not projected out of any of the data, it can still be employed in calculating the calibration by using an additive noise term as in step 178 of FIG. 3. The objective of effectively using the spectral information that is available a priori need not be relinquished.

In some instances, the concentration of the analyte cannot be readily ascertained by independent means from exactly the same volume in the sample from which the spectra is obtained. An example of such a case occurs for noninvasive glucose measurements in human skin by spectroscopy. The method of independent measurement often relies on blood samples but blood is not a dominant constituent of the human skin. The bulk of the glucose in human skin, measurable by some spectroscopic methods, is dissolved in the interstitial fluid. The relationship between the glucose in the blood and that in the interstitial fluid is determined by diffusion of glucose across blood vessel walls, and by the uptake of glucose from the interstitial fluid by the living cells of the skin. From the foregoing it can be seen that a calibration error could result from using the unmodified blood glucose concentrations.

A model is proposed which in practice has been found to sufficiently correct for the differing concentrations in the interstitial fluid and the blood. Let:

r, be the fraction of the glucose in the skin which is dissolved in the blood, $t_f$, is the time constant associated with dropping blood glucose being reflected in dropping glucose concentration in the interstitial fluid, $t_r$, is the time constant associated with rising blood glucose being reflected in rising glucose concentration in the interstitial fluid, C is the consumption rate by the tissue of glucose;

Y is the measured blood glucose as a function of time;

$Y_{if}$ is the glucose concentration of glucose in the interstitial fluid as a function of time;

and $Y_d$ is the volume averaged glucose in the skin as a function of time.

We propose a linear model where:

$$Y_{if} = Y(0) + \int_0^t \left[ \frac{(Y-Y_{if})\theta(Y-Y_{if})}{t_r} + \frac{(Y-Y_{if})\theta(Y_{if}-Y)}{t_r} \right] dt - Ct - Ct_r \quad (15)$$

$$Y_d = rY + (1-r)(Y_{if} + Ct_r) \quad (16)$$

where θ is the Heaviside function defined as Θ(t)=1 for t>0 and, Θ(t)=0 for t<0, where t is the time and t=0 is the time at which the measurements commence.

Figure 5:
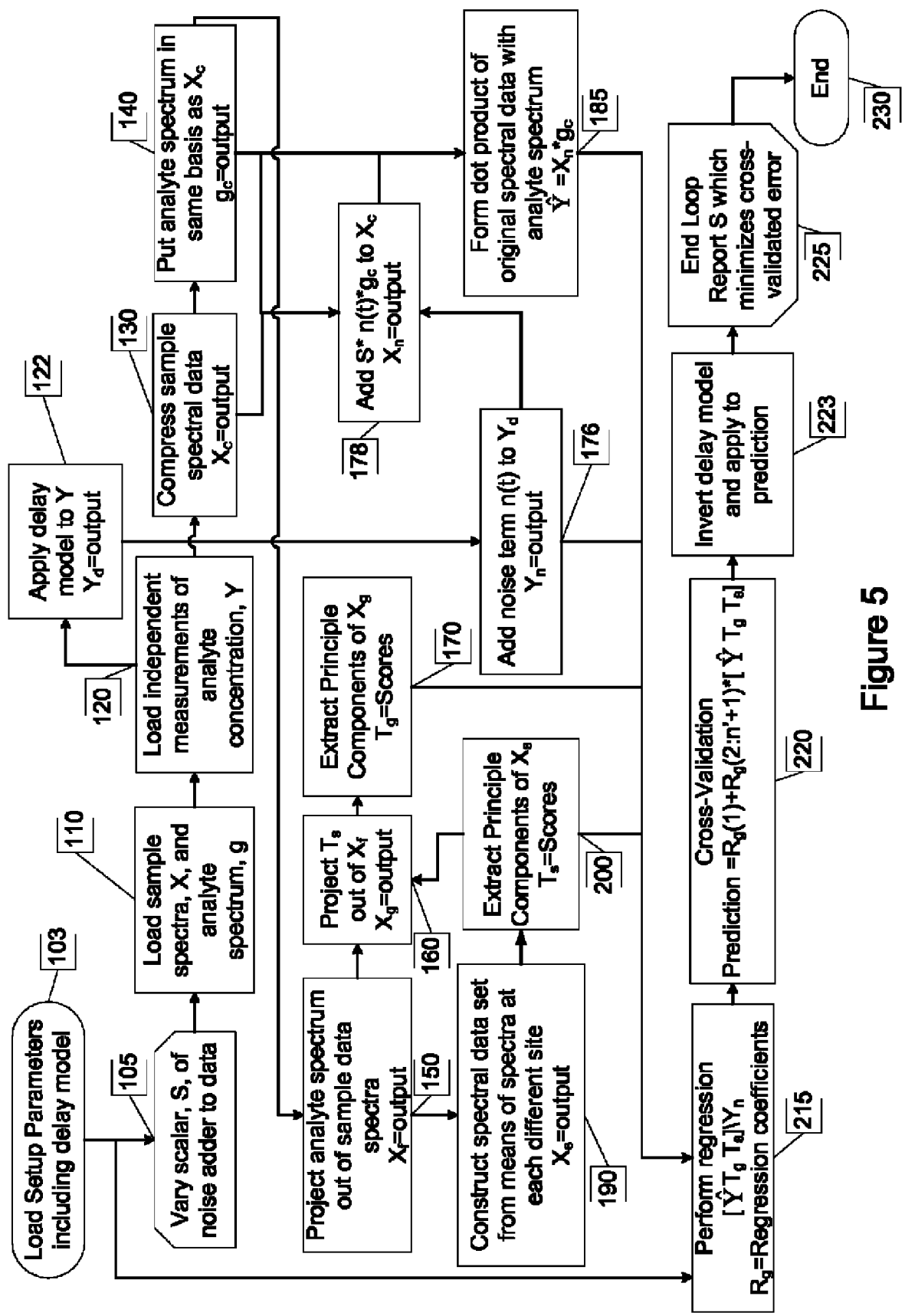
FIG. 5 shows another preferred embodiment where the independent measurements of the analyte concentration are modified on the basis of expected systematic differences between the samples measured by the independent apparatus and those measured by the spectroscopic apparatus.

The computation is presented in FIG. 5, where the model of Eqs. 15 and 16 is implemented in step 122, and thereafter, $Y_d$ is used where Y had previously used, as shown in step 176.

This delay model allows different rise and fall times based on reports in the literature. The effect of non-negligible values of $t_{r,f}$ is to reduce the rate of change of the volume averaged glucose with respect to the rate of change of the blood glucose, and to reduce the amplitude of glucose excursions associated with the change. It is found empirically that the values of $t_{r,f}$ are of the order of 10 minutes and that r<0.25. It is of course possible to optimize all 4 parameters ($t_r$, $t_f$, r, and C), to minimize the cross-validation error which is computed in step 220 of FIG. 5. This may be done on a single individual subject or on data from multiple subjects.

In addition, the cross-validated predictions that emerge from step 220, can be systematically corrected by inverting the delay model of Eqs. 15, and 16 and applying the inverse to the predictions, as is shown in step 223 of FIG. 5. In the cross-validation, we are not entitled to know any of the future data. In this case, the inverted delay model is applied to the historical data and to the new prediction. Changes in either direction will be exaggerated, and excursions in either direction will increase in amplitude. It is possible to put reasonable physical limits on the slopes of these changes on the basis of known limitations on the rate of change of the analyte concentration. For example, we can require that the rate of change of a blood glucose prediction be less than 4 mg/dL/min. The algorithm would apply the inverted delay model but default to the maximum rate of change if the inverted delay model predicted a change greater than that which is physically possible.

It is also clear from the foregoing that it is advantageous to use $Y_d$ instead of Y for the case of noninvasive glucose testing, if the analyte concentration is projected out of any of the data, as in Eq. 9.

In some circumstances, substances that have spectra that are partially colinear to the analyte spectrum may contribute substantially to the estimate of $\hat{Y}$ in Eq. 4. This is particularly likely if the concentrations of substances whose spectra are colinear with the analyte are higher than that of the analyte. In such circumstances, it is possible to improve the estimate by reducing the contributions from these interfering substances. We begin by writing a figure of merit, F, as follows:

$$F = \{(r^*g_c)^2 - A^*[(r^*X_c^t)^*(X_c^*r)]\}/(r^*r) \quad (17)$$

where r is a revised spectrum for the analyte, A is a constant, and $X_c^t$ is the transpose of $X_c$. The objective of Eq. 17 is two-fold, and is to maximize the overlap of r with the original analyte spectrum $g_c$, but to minimize the overlap of r with that of the data $X_c$. The reason for the latter objective is specific to systems in which it is known that the spectra of the mixture contains more signal which is colinear to the analyte spectrum from substances other than the analyte, than it does from the analyte itself. By minimizing F, a suitable compromise between these objectives can be found. Taking the derivative of Eq. 17 with respect to r, and setting it equal to 0, enables one to find the following expression:

$$r_j = g_{cj}/(1 + C_1 * \|T_j\|^2) \quad (18)$$

where the subscript j refers to the jth component in the basis of the loadings of the principle components of X, the T's are the scores of the principle components of X, and $C_1$ is a constant. A method which implements Eq. 18 is presented in FIG. 6 with inputs T, $g_c$, and $C_1$. From step 176, Eq. 18 can be solved for $r_j$ in step 179.

Figure 6:
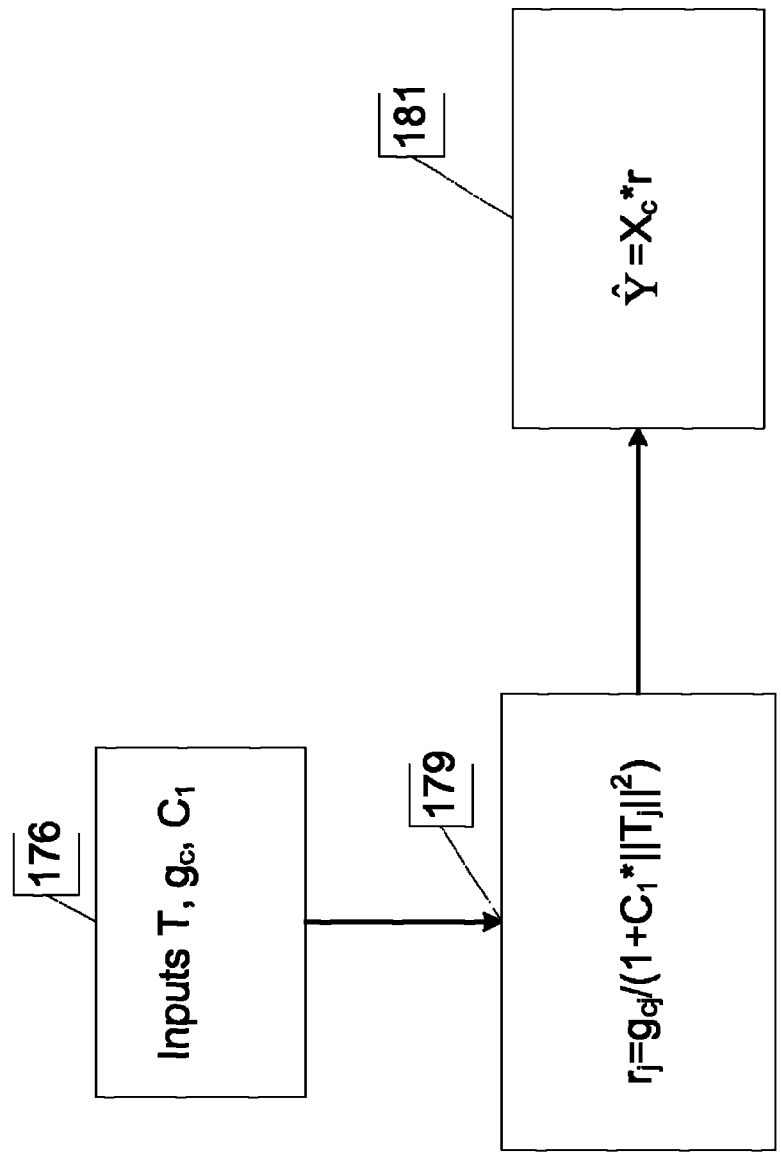
FIG. 6 is a particularly preferred embodiment when the spectra are dominated by substances that interfere with that of the analyte, and wherein a revised analyte spectrum is computed to improve the estimation of the analyte concentration.

Having constructed the revised analyte spectrum, we can compute a new $\hat{Y}$ according to step 181 of FIG. 6, $$\hat{Y} = X_c * r \quad (19)$$

In a particularly preferred embodiment, for those cases in which the analyte concentration is small compared to that of the interfering substances, the $\hat{Y}$ of Eq. 19 can be used in preference to the $\hat{Y}$ of Eq. 4, in step 180 of FIG. 2 or 4. Similarly, r can be substituted for $g_c$ in step 185 of FIG. 3 or 5. The constant $C_1$ in Eq. 18 can be chosen so as to minimize the error of the cross-validated prediction of the analyte concentration. It has been found in practice that this is beneficial.

A spectrum consists of signal amplitudes at various wavelengths. It is sometimes the case that the inclusion of a subset of the spectral data, at some subset of wavelengths, will actually give rise to errors in the prediction of the analyte concentration that are larger than if the subset had been excluded. At some wavelengths the analyte may have weak signal compared to that of other substances in the mixture. It is not necessarily disadvantageous to include these wavelengths in the analysis as inclusion may sometimes enable a better estimate of the spectral contribution of other substances which contribution may then be more accurately extracted. It is, however, sometimes the case, that inclusion of some wavelengths is deleterious. A simple example of such a case is when the signal consists of random noise at these wavelengths.

Figure 7:
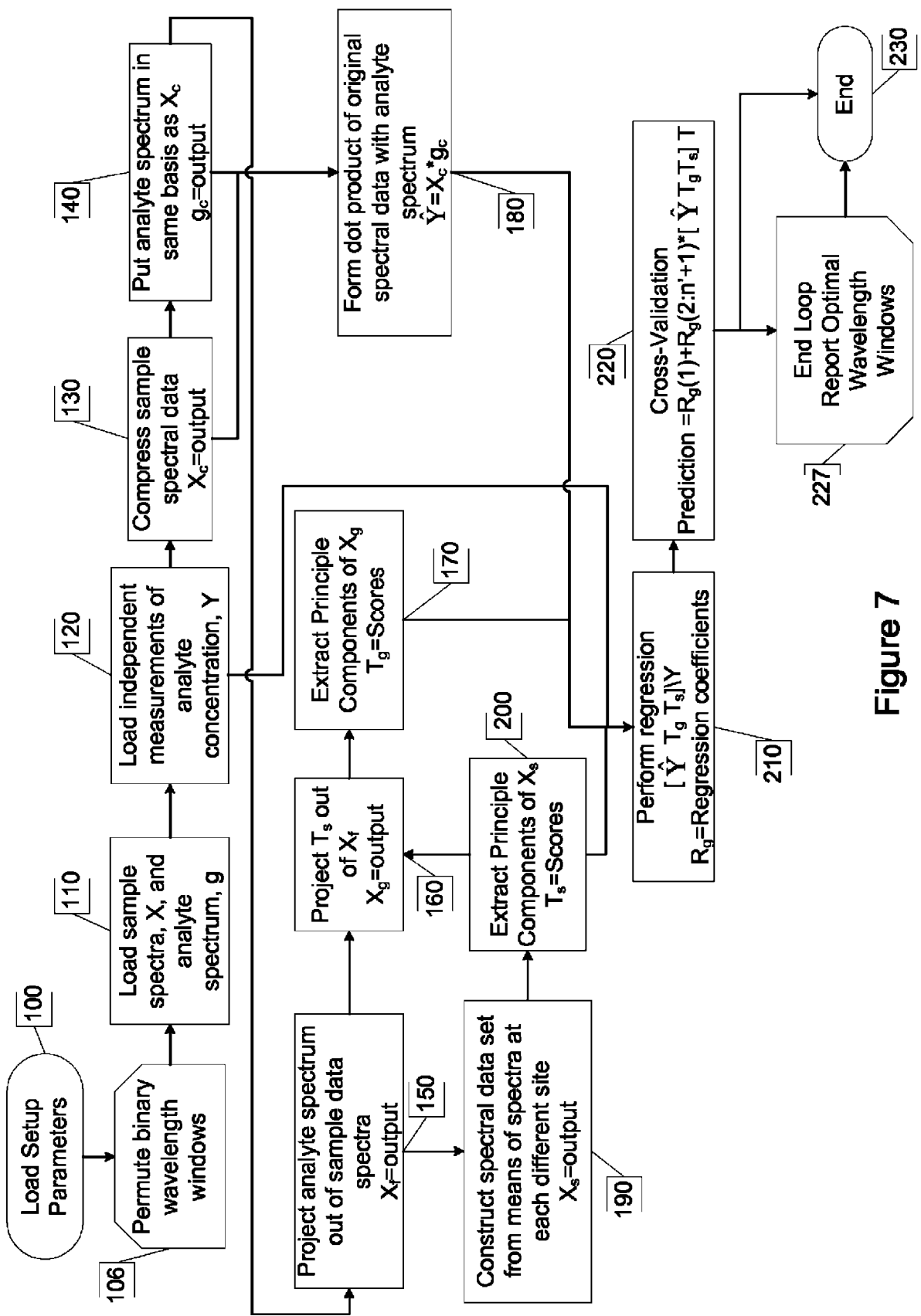
FIG. 7 is yet another preferred embodiment wherein the spectral data is filtered by including or excluding a multiplicity of spectral windows.

It is possible to systematically choose the wavelengths to be included in the analysis on the basis of finding the subset which gives the best cross-validated error of prediction. A convenient way of proceeding is to divide the spectrum into $n_s$ segments, which need not be of equal size. It is possible then to exclude or include the data from each segment by multiplying the spectral data in that window either by a 0 or a 1. The cross-validated prediction error of the analyte concentration can be compared with any window either included or excluded. If the cross-validated prediction error goes down, the inclusion or exclusion can be decided on the basis of which choice produced the smaller error. This operation can be carried out for each window. This method is illustrated in FIG. 7, where a loop which permutes the on and off states of each window is initiated in step 106, and the loop is terminated in step 227, where the window choices which minimized the cross-validated prediction error are reported. The sequence can start from a state where all the windows are included, but this is not an essential feature. It also can be repeated several times and executed beginning with windows at smaller wavelengths and proceeding to windows at larger wavelengths or vice versa. Any of the methods illustrated in FIGS. 2-6 can be nested within the wavelength window optimization loop. If the computational power available is adequate, the method illustrated in FIG. 7 can examine the case of turning windows on and off two or more at a time in all combinations, which may improve the outcome.

Other optimization algorithms whose objective is to minimize the cross-validated error of prediction for the wavelength windows can be used with any of the methods of FIGS. 2-6. Examples are simulated annealing, and genetic algorithms.

When dealing with live subjects, the site on which the measurement is made may change because the subject moves. These motions can be either deliberate, in which case the change can be noted by an operator, or it may be inadvertent. The method of FIG. 2 attempts to extract the effect of site to site variance by creating a data set consisting of some number of spectra taken at each distinct site. The scores, $T_s$, associated with the principle components are vectors having the dimension of the number of sites. To perform step 160 of FIG. 2, it is necessary that the dimension of the $T_s$'s must be the same as the number of spectra in $X_f$. In step 190 of FIG. 1, however, we compute a data set $X_s$, which consists of only a single spectrum at each site (or equivalently for each sample). It is often advantageous, however, that multiple spectra be taken at each site, hence, the data set $X_f$ often consists of multiple spectra at each site and will therefore have dimension greater than $T_s$. In the case where the $X_f$ has larger dimension than the $T_s$'s, the values of the $T_s$'s computed for each site are duplicated as many times as necessary so that the number of values of each $T_s$ at each site is the same as the number of spectra at each site in $X_f$.

A case can arise when dealing with mobile subjects, where the site of the measurement may change without intent. An example of such a situation would be where a human subject moves inadvertently. A motion of sufficient magnitude, is equivalent to moving to a new distinct site. In such circumstances, it may not be correct to duplicate the $T_s$ values to have the same dimension as the $X_f$ at each site because, in actuality, there were more sites assessed than were reported, and the duplicate values of the $T_s$'s may not be correct if the site changed. From the foregoing, it is clear that it is advantageous to find a method whereby a change of site can be automatically identified from the data, without the requirement that any human be cognizant of it at the time which it transpires.

We have previously constructed the data set $X_s$ in step 190 of FIG. 2. Let $P_s$ be the loadings of the principle components of $X_s$. Referring now to step 203 of FIG. 8a, we calculate $S_t$ as follows:

$$S_t = X_c * P_s \qquad (20)$$

Essentially the $S_t$'s tell us what portion of the spectral data, $X_c$, is colinear with the spectra, $P_s$. The spectra $P_s$ capture the site to site or sample to sample variance, not associated with variations in the analyte concentration, since they are loadings of the principle components of $X_s$. Therefore, the $S_t$'s will contain the proper information to ascertain a change in site. In particular, if the site is changed, a discontinuity in the $S_t$'s will likely be observed.

Next, the discontinuities in the $S_t$'s are detected as is shown in step 204 of FIG. 8a. We begin by finding the difference between the neighboring $S_t$'s:

$$S_1 = S_t(t+\Delta t, i) - S_t(t, i) \qquad (21)$$

where the $S_t$ are ordered series, which for instance can be time series, and t is the designation for series, and $\Delta t$ is an increment in the series. For example t could be 10 minutes, and $\Delta t$ could be 1 minute, or t could be series 25, and $\Delta t$ could be 1 series. In Eq. 18, i refers to the ith component, and the maximum value of i is the same as the number of $P_s$'s, which we will take to be NP. A normalized version of $S_1$ is now created:

$$S_2 = S_1 / (\int \|S_1(t,i)\|^2 dt)^{0.5} \qquad (22)$$

The test of step 204 in FIG. 8a is then:

$$\sum_{i=1}^{NP} |S_2(t, i)| > Th \qquad (23)$$

where Th is a threshold for the Yes/No decision.

If step 204 provides a 'yes' decision, then it is further necessary to ascertain whether assignment of the spectral data to an additional site will potentially create an excessively small series of spectra for that prospective additional site. As an example, in a given situation we might find that we need at least 10 spectra to give adequate signal to noise ratio to accurately assess the analyte concentration. Suppose that data associated with the previous site assignment began at spectrum #25, and that we now detect a discontinuity at spectrum #32. If we assigned data beginning with spectrum #32 to a new site, we would only have 7 spectra associated with the previous site, which in this example would not meet our requirement for a minimum of 10. Furthermore, it is possible that the prospective assignment will not have enough series. In either such case, we could choose to keep the original assignments, the decision for which is provided in step 207 of FIG. 8a. If the number of series assigned both to the prospective site, and the prior site is satisfactory, then the data are assigned to the additional site, per step 208. If, by virtue of the prospective assignment, the number of data series associated with either the prospective or prior assignment falls below the requirement, the prospective assignment can be rejected, as in step 209.

The example method of FIG. 8a is a suitable general tool for detecting when a sample has changed significantly due to causes not associated with a change in analyte concentration. Although its function was illustrated by using an example of different sites on biological organisms capable of motion, it is not limited to this case. It is sufficient to use the algorithm that the set $X_s$ in FIG. 2 can be created, where the set $X_s$ is representative of the variations of the spectra between samples, and either the analyte spectrum or its concentration has first been projected out of the data from which $X_s$ was calculated.

In some systems where photo-bleaching is observed as a result of the illumination of the sample by the optical source, another approach is possible to detect physical motion. When motion occurs over a range that is a non-negligible fraction of the diameter of the spot produced by the optical source on the sample, an increase in fluorescence may be detected. That is because a fresh area of the sample that has not yet been subject to photo-bleaching is now illuminated by the optical source, hence the process of absorption and emission of fluorescence has not been inhibited by the bleaching. A method which makes use of this phenomenon is presented in FIG. 8b. A suitable spectral window is chosen over which the fluorescence signal is averaged as in step 112. Discontinuous changes are detected in step 114, by comparing neighboring averaged fluorescence signals. A new site may be assigned if the discontinuity is of sufficient magnitude as in step 119. If not, the original assignment is accepted as in step 117. Considerations of whether series of adequate length can of course be handled as in steps 207, 208, and 209 of FIG. 8a, if desired.

Figure 9:
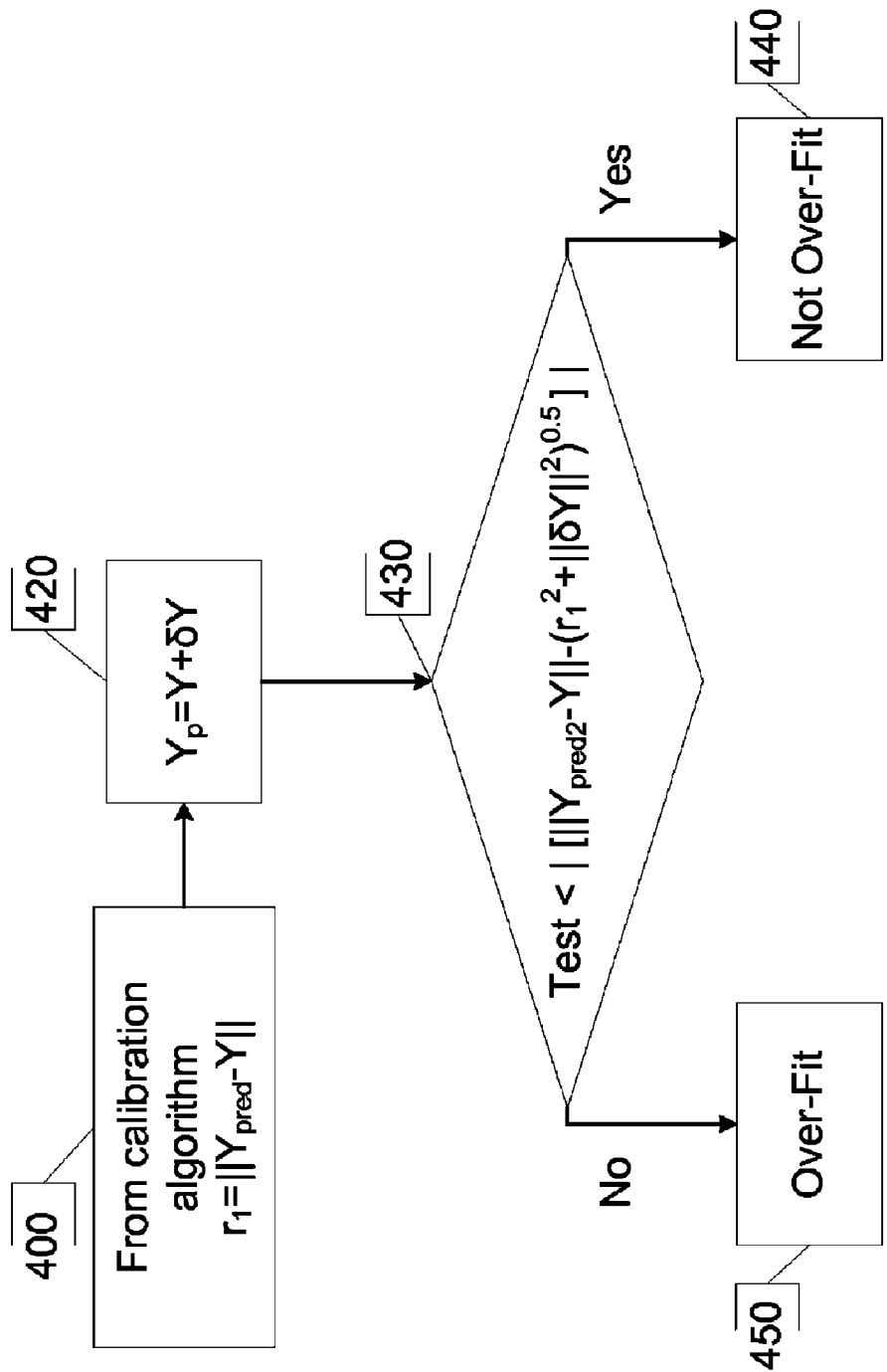
FIG. 9 is an algorithm which is designed to test whether the calibration algorithm has over-fit the data.

After running any calibration algorithm, it is highly desirable to test the solution to ascertain whether over-fitting has occurred. An algorithm for making such a test is proposed in FIG. 9. First, the error of prediction from running the calibration algorithm is provided as input in step 400:

$$r_1 = \|Y_{pred} - Y\| \quad (24)$$

where $Y_{pred}$ is the calculated prediction of the analyte concentration, and Y is the actual analyte concentration.

In step 420, a perturbation $\delta Y$ is added to the analyte concentration Y:

$$Y_p = Y + \delta Y \quad (25)$$

The perturbation, $\delta Y$ is advantageously chosen to be a sine function. In one embodiment, the wavelength of the perturbation is best chosen such that the maximum derivative of $\delta Y$, normalized to the amplitude of the perturbation, is similar in magnitude to the maximum derivative of Y, normalized to the variance of Y. Let $Y_{pred2}$ be the prediction produced by the algorithm when Y is replaced with $Y_p$, the perturbed Y. The method now tests to find whether the error of the new estimate associated with the propagation of the perturbation $\delta Y$ through the calibration algorithm, has increased according to expectations. The appropriate test is given in step 430 and is:

$$|[\|Y_{pred2} - Y\| - (r_1^2 + \|\delta Y\|^2)^{0.5}]| < \text{Test} \quad (26)$$

where Test is the threshold for declaring the model over-fit and is advantageously chosen to be much less than the amplitude of $\delta Y$. If the test is true, then the data has not been over-fit as shown in step 440. If the test is false then the data is over-fit as shown in step 450.

The proposed test is independent of the algorithm used for calibration, and algorithms different from those proposed in FIGS. 2-7 may be used to create the necessary inputs for Eqs. 24 and 26.

One noteworthy feature of the proposed algorithm is that the regression vector used in calibration depends on the choice of both the training and the test data. In actual application, the training set would be spectra taken under conditions for which the analyte concentration is known from an independent reference meter. For example, for the case of blood glucose determination in humans, the reference data might be from an invasive meter that measures the glucose concentration using glucose oxidase reactions. Either all of the available reference data would be used in constructing a training set, or the training set would be advantageously chosen to be a particular subset of the available reference data. This subset might be, for example, chosen to remove outliers, chosen to optimize the cross-validation, chosen to minimize the size of the training set, or chosen to best model the observed variance in the training set.

The test set could be chosen either as a single measurement $X_{test}$, or perhaps advantageously chosen to also include a set of measurements $X_{extra}$ that represent either sample to sample variation or variation within the same sample as $X_{test}$; as explained in Section 20. Because the regression produced by calibration depends globally on the test set, these choices may be advantageous in some instances. $X_{extra}$ may be chosen using, e.g., a classifier scheme or expert system, in order to optimize the quality and reliability of the predictions over the course of a continuous measurement made over a long period of time. Because data on, e.g., a human subject are correlated in time, it may also be advantageous to choose $X_{extra}$ from among recent prior measurements.

The above description is included to illustrate the operation of the embodiments and is not meant to limit the scope of the invention. From the above discussion, many variations will be apparent to one skilled in the relevant art that would yet be encompassed by the spirit and scope of the invention. Those of skill in the art will also appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Some portions of the above description present the features of the present invention in terms of methods and symbolic representations of operations on information. These descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of a method. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for enablement and best mode of the present invention.

The invention claimed is:

1. A method for estimating a target analyte concentration from a test spectrum collected from a sample, the method comprising:
   accessing a first spectral data set that includes a plurality of spectra collected from first samples, the first spectral data set including a training data set of training spectra and a test data set of test spectra;
   accessing independently measured target analyte concentrations corresponding to the training spectra, the independently measured target analyte concentrations collected from second samples different than the first samples;
   generating modified measured target analyte concentrations from the independently measured target analyte concentrations by applying a delay model that converts concentrations from the second samples to corresponding concentrations from the first samples;
   generating a model that predicts target analyte concentration based on a test spectrum, the model generated based at least in part on the first spectral data set and on the modified measured target analyte concentrations; and
   applying the model to the test spectrum to estimate the target analyte concentration.

2. The method of claim 1 wherein the delay model includes a rise time for rising values of the target analyte concentration in the second sample and a different fall time for falling values of the target analyte concentration in the second sample.

3. The method of claim 1 wherein the delay model represents the relationship between the modified measured target analyte concentrations and the independently measured target analyte concentrations by a linear differential equation.

4. The method of claim 1 further comprising:
   applying an inverse of the delay model to the estimated target analyte concentrations.

5. The method of claim 1 wherein:
   the target analyte is glucose;
   the first spectral data set is collected by non-invasive spectroscopic measurement of glucose in human skin;
   the independently measured target analyte concentrations are collected by measurements of glucose in blood samples; and
   the delay model accounts for diffusion of glucose from the blood into the human skin.

6. The method of claim 1 wherein the target analyte is blood glucose.

7. The method of claim 6 wherein the spectra are collected by Raman spectroscopy.

8. The method of claim 6 wherein the training data set comprises training spectra collected from at least three different samples.

9. The method of claim 6 wherein the training data set comprises training spectra collected from at least six different samples.

10. The method of claim 6 wherein the independently measured target analyte concentrations for the training spectra span a range of at least 50 mg/dL.

11. The method of claim 6 wherein the independently measured target analyte concentrations for the training spectra span a range of at least 100 mg/dL.

12. The method of claim 6 wherein the spectra are collected from different sites, and different sites are considered to be different samples.

13. The method of claim 12 further comprising:
   determining whether a site should be considered to be more than one sample based on variations in the spectra collected from the site.

14. The method of claim 1 further comprising:
   selecting a subset of wavelengths of the wavelengths collected from different samples, for use in the spectral data sets.

15. The method of claim 1 further comprising:
   determining whether overfitting has occurred in generating the model by adding a perturbation to the independently measured analyte concentrations and ascertaining whether additional error in estimating the analyte concentrations from the spectra is consistent with the magnitude of the added perturbation.

16. A system for estimating a target analyte concentration from a test spectrum collected from a sample, the system comprising:
   means for accessing a first spectral data set that includes a plurality of spectra collected from first samples, the first spectral data set including a training data set of training spectra and a test data set of test spectra;
   means for accessing independently measured target analyte concentrations corresponding to the training spectra, the independently measured target analyte concentrations collected from second samples different than the first samples;
   means for generating modified measured target analyte concentrations from the independently measured target analyte concentrations by applying a delay model that converts concentrations from the second samples to corresponding concentrations from the first samples;
   means for generating a model that predicts target analyte concentration based on a test spectrum, the model generated based at least in part on the first spectral data set and on the modified measured target analyte concentrations; and
   means for applying the model to the test spectrum to estimate the target analyte concentration.

17. The system of claim 16 wherein the delay model includes a rise time for rising values of the target analyte concentration in the second sample and a different fall time for falling values of the target analyte concentration in the second sample.

18. The system of claim 16 wherein the delay model represents the relationship between the modified measured target analyte concentrations and the independently measured target analyte concentrations by a linear differential equation.

19. The system of claim 16 further comprising:
means for applying an inverse of the delay model to the estimated target analyte concentrations.

20. The system of claim 16 wherein:
the target analyte is glucose;
the first spectral data set is collected by non-invasive spectroscopic measurement of glucose in human skin;
the independently measured target analyte concentrations are collected by measurements of glucose in blood samples; and
the delay model accounts for diffusion of glucose from the blood into the human skin.

* * * * *